US006990371B2

(12) United States Patent
Powers et al.

(10) Patent No.: US 6,990,371 B2
(45) Date of Patent: Jan. 24, 2006

(54) METHOD AND APPARATUS FOR PROVIDING ON-SCREEN INCIDENT REVIEW IN AN AED

(75) Inventors: Daniel J Powers, Issaquah, WA (US); Karl A Woelfer, Seattle, WA (US); Judith L Cyrus, Preston, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 317 days.

(21) Appl. No.: 09/418,536

(22) Filed: Oct. 14, 1999

(65) Prior Publication Data

US 2002/0156503 A1    Oct. 24, 2002

(51) Int. Cl.
*A61N 1/378*    (2006.01)
(52) U.S. Cl. .......................................... 600/510; 607/5
(58) Field of Classification Search .............. 600/510, 600/523, 525; 607/4, 5, 7, 59
See application file for complete search history.

(56) References Cited

U.S. PATENT DOCUMENTS

| 4,610,254 | A  |   | 9/1986  | Morgan et al. |
| 4,945,477 | A  |   | 7/1990  | Edwards |
| 5,345,552 | A  | * | 9/1994  | Brown ........................ 395/157 |
| 5,549,115 | A  | * | 8/1996  | Morgan et al. ............. 128/696 |
| 5,607,454 | A  |   | 3/1997  | Cameron et al. |
| 5,683,423 | A  | * | 11/1997 | Post .............................. 607/5 |
| 5,785,043 | A  | * | 7/1998  | Cyrus et al. ................ 128/712 |
| 5,836,993 | A  |   | 11/1998 | Cole |
| 5,879,374 | A  | * | 3/1999  | Powers et al. ................. 607/5 |
| 6,108,578 | A  | * | 8/2000  | Bardy et al. ................... 607/5 |
| 6,141,584 | A  | * | 10/2000 | Rockwell et al. .............. 607/5 |
| 6,201,992 | B1 | * | 3/2001  | Freeman ........................ 607/5 |
| 6,292,692 | B1 | * | 9/2001  | Skelton et al. ................. 607/5 |

FOREIGN PATENT DOCUMENTS

WO    WO94/27674    12/1994

* cited by examiner

*Primary Examiner*—Robert E. Pezzuto
*Assistant Examiner*—Frances P. Oropeza
(74) *Attorney, Agent, or Firm*—Tony Piotrowski

(57) ABSTRACT

A novel apparatus and method for recording and replaying patient treatment and response data that occurs during the course of an emergency response on a defibrillator. The data and events of an emergency response may be recorded automatically by the defibrillator. Incidents may then be randomly accessible (i.e. "scrollable") by medical personnel on the defibrillator by placing the defibrillator into an incident review mode. The ability to quickly review critical ECG and event data on the scene. This provides medical personnel with a reliable and efficient alternative to paper based recording systems.

27 Claims, 4 Drawing Sheets

METHOD AND APPARATUS FOR PROVIDING ON-SCREEN INCIDENT REVIEW IN AN AED

FIELD OF THE INVENTION

The present invention relates in general to defibrillators, particularly automatic or semi-automatic external defibrillators ("AED"). In particularly, this invention relates to a method of providing for on-screen review for an AED.

BACKGROUND OF THE INVENTION

Sudden cardiac death is the leading cause of death in the United States, with one person dying every two minutes. Most sudden cardiac death is caused by ventricular fibrillation ("VF"), in which the heart's muscle fibers contract without coordination, thereby interrupting normal blood flow to the body. The only known effective treatment for VF is electrical defibrillation, in which an electrical pulse is applied to the patient's heart. The electrical pulse must be delivered within a short time after onset of VF in order for the patient to have any reasonable chance of survival. Electrical defibrillation may also be used to treat shockable ventricular tachycardia ("VT"). Accordingly, defibrillation is the appropriate therapy for any shockable rhythm, i.e., VF or shockable VT.

One way of providing electrical defibrillation uses an external defibrillator. External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators (referred to collectively as "AEDs") are becoming increasingly popular because they can be used by relatively inexperienced personnel. Such AEDs are also especially lightweight, compact, and portable. AEDs are described in U.S. Pat. No. 5,607,454 to Cameron et al. entitled "Electrotherapy Method and Apparatus" and PCT Publication No. WO 94/27674 entitled "Defibrillator with Self-Test Features", the specifications of which are incorporated herein.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, etc. Because AEDs are designed to be small, lightweight and easy to maintain, AEDs generally do not feature a paper based ECG recorder.

One drawback to using an AED is that it typically does not provide a way to review the historical ECG data since AEDs display only the currently monitored information. ECG review is accomplished via a paper-based ECG print-out. Because of the added weight associated with an ECG printer this is a feature that is typically included in the larger multi-feature defibrillators (for example, the CodeMaster 100 by Hewlett-Packard). As AEDs have become more common (e.g. in airports, hotels, cruise ships, and airplanes), the number of times responsibility for the care of a victim is transferred increases. For example, instead of the traditional paramedic to emergency room transfer, the situation now exists where a first responder (such as a lay person, or airline attendant) may be superceded by a firefighter or police officer and then a paramedic prior to being taken to the emergency room at a hospital. Each time responsibility for a patient is handed off to a more advanced caregiver, it is important to be able to quickly transfer relevant historical treatment information. However, while professional caregivers are accustomed to providing a thumbnail summary of prior treatment to an advanced caregiver, such as an emergency room physician, the same is not true for a lay responder.

Thus, when emergency response personnel are called to the scene of a cardiac arrest or a patient is transferred to the emergency room, the ability to quickly review the incident (or ECG history) is desirable since the initial lay responder may not be in a position to accurately describe the early portions of the treatment. This is particularly important, because ECG history can impact subsequent treatment. Further, it is desirable to note the various treatments applied at the scene and record the patient's response. Such information might help trained cardiologists, reviewing the information, to rule out certain disease or defect conditions that potentially could afflict the patient prior to administering treatment.

U.S. Pat. No. 4,610,254 to Morgan et al. for "Interactive Portable Defibrillator," discloses a portable interactive defibrillator that records patient status information such as ECG as well as user-supplied information that is input in the form of prompts from the defibrillator to the user. Morgan further discloses the use of a tape recorder medium to record relevant medical information during the use of device. The recorder is a two-track recorder—one track for ECG and other patient data and the second track for audio data to record the voice of the response personnel as well as sounds indicating that a shock has been delivered to the patient. The tape recorder allows the data to be removed from the device for subsequent review.

U.S. Pat. No. 4,945,477 to Edwards for "Medical Information System," discloses a system for recording and presenting information pertaining to a medical event such a cardiac arrest. Edwards' system records events identified by the defibrillator and stores these events for human-readable replay. Defibrillator-identified events (termed "annotations") can be effected by the pressing of a button on the defibrillator by the user or by the recognition that a medical event (e.g. arrhythmia) has occurred. As a memory space saving technique, Edwards describes a means in which his system stores three second intervals according to priority of events. Events having higher priority may well overwrite events of lower priority.

U.S. Pat. No. 5,785,043 to Cyrus et al. for "Method of Creating A Report Showing a Time Correlation Between Recorded Medical Events," describes a system for retrieving and presenting information recorded by an AED on a personal computer.

While these systems do provide some level of data recording and subsequent play-back, they do not provide a mechanism to play back information recorded during treatment of a patient on the device screen. Further, there is no provision for review of the data while the device is still connected to a patient.

Thus, it is an object of the present invention to provide medical personnel with an AED that allows the user to review the recorded data on the device. Ideally, this information can be reviewed both on-line (i.e., when the device is attached to the patient) or off-line (after the device has been used to treat the patient).

SUMMARY OF THE INVENTION

A method of reviewing incident data on an external defibrillator comprising: deploying the defibrillator for use in an emergency, wherein the defibrillator is attached to a patient; monitoring ECG data from the patient; recording the monitored ECG data in memory; and activating an incident review mode. The method further comprises: retrieving the recorded ECG data from memory; and replaying the recorded ECG memory on a visual image generator. The activating step may be accomplished by user intervention. Further, the replaying step may occur automatically without user actuation of an activation button. The recording step may include recording audible data received from a microphone into memory. The replaying step may further comprises replaying the audible data recorded into memory during the recording step. Prior to replaying, the user may select which information is replayed. In that case, the user would select, for example, from the group consisting of: ECG data, audible data, and a combination of ECG and audible data. Further, ECG data would be selected from the group consisting of: patient ECG data, and patient therapy data. The replaying step may be activated by the user depressing soft keys or a combination of soft keys. Alternatively, incident review mode is activated in response to disconnecting the patient from the defibrillator or insertion of a new battery. While in incident review mode, a legend should be displayed on a visual image generator that the defibrillator is in event review mode. The replaying option may be presented to the user when the instrument is turned off. Under a preferred embodiment, the defibrillator continues to monitor patient ECG. In this instance, it is also possible to display the currently monitored ECG data along with the recorded ECG data retrieved from memory.

An external defibrillator comprising: a controller, an energy delivery system operable by the controller to deliver an electrical shock from an energy source to an electrode interface; memory for recording incident data; an incident review activator; and an incident review output comprising a visual image generator, wherein the incident review output retrieves incident data from memory upon activation of the incident review activator by the user. Memory would be selected from the group consisting of removable memory and integral memory, specifically, flash, EEPROM, ROM and RAM. In this external defibrillator the incident review output also comprises an audible sound generator. The incident review activator is a soft key or a combination of soft keys. Incident review navigators may also be provided. The benefit of the navigators is that it enables the user to advance or replay the incident. Incident review navigators may be a soft key or a combination of soft keys.

DETAILED DESCRIPTION OF THE INVENTION

The following discussion is presented to enable a person skilled in the art to make and use the invention. Various modifications to the preferred embodiment will be readily apparent to those skilled in the art, and the generic principles defined herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
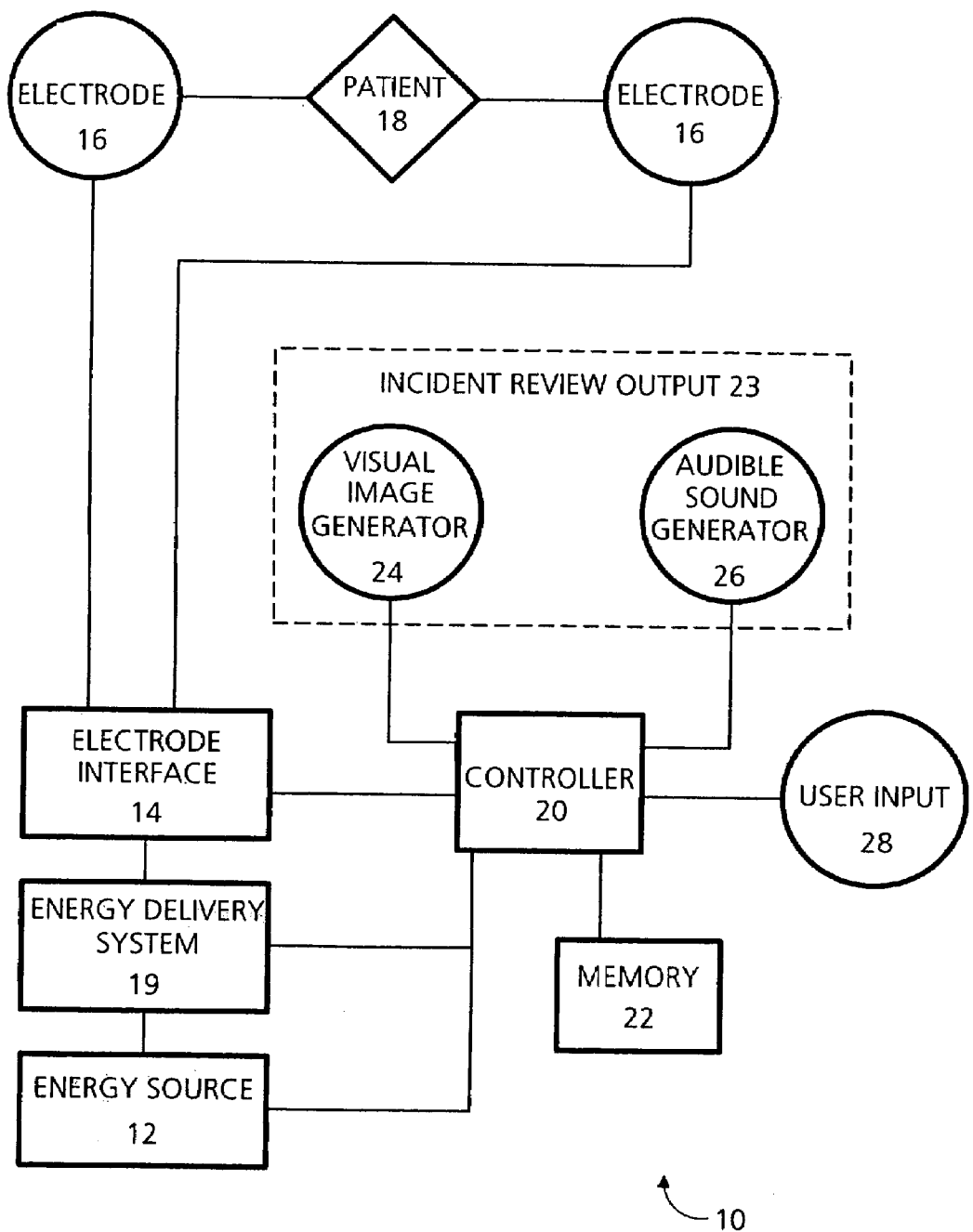
FIG. 1 is a block diagram of an electrotherapy device that might be suitable to employ the methods of the present invention.

FIG. 1 is a schematic block diagram of a defibrillator system 10 according to a preferred embodiment of this invention. The defibrillator system 10 comprises an energy source 12 to provide voltage or current pulses. A controller 20 operates an energy delivery system 19 to selectively connect and disconnect energy source 12 to and from a pair of electrodes 16 electrically attached to a patient 18 through an electrode interface 14 to provide electrotherapy to the patient. The defibrillator system 10 is an electrotherapy device such as a manual defibrillator or AED. Alternatively, defibrillator system 10 may be a defibrillator trainer that simulates the behavior of a manual or automatic/semi-automatic defibrillator in use, in which case the electrode interface and energy delivery system may be omitted.

Memory 22 records data collected by the defibrillator while monitoring and treating a patient. Data received with respect to a particular patient's monitoring and treatment is referred to as an "incident." An incident consists of, for example, discrete events and continuous or non-continuous ECG data. Importantly recorded data may be appended to previously recorded data under appropriate conditions. For example, when a device is deployed to treat a patient, in the event the device were turned off (for example, to replace the battery), the data recorded after the device is turned on would, under some circumstances, be appended to the previously recorded data. Thus, the recorded incident would comprise discrete non-continuous data recorded in connection with a perceived continued use. Alternatively, non-continuous data could result where only a portion of the data received is recorded (for example, data windows around relevant events, e.g. 5 seconds before and after a shock decision). Memory 22 may include any appropriate memory device such as FLASH, EEPROM, ROM or RAM. Memory 22 may be removable or, alternatively, may be integral with the defibrillator.

The incident may be reviewed by a subsequent caregiver through an incident review output 23, which consists in this embodiment of a visual image generator 24 and an audible sound generator 26. Visual image generator 24 may display, among other things, current ECG, ECG history, etc. The visual image generator 24 may be, for example, a liquid crystal display ("LCD"). Additionally, an audible sound generator 26 may be provided that broadcasts any the corresponding voice recording that was made at the time the ECG data was recorded. Activation of the visual image generator 24 and the audible sound generator 26 is controlled by the controller 20 in response to the information received from memory 22.

Additionally, in a preferred embodiment, user input 28 is provided to interact with the memory 22 to control the incident review. For example, user input is provided in order to enable the user to cease the active monitoring/therapy operation of the defibrillator and to begin the incident review. Additionally user input is provided in order to allow the caregiver to navigate through incident data; advancing or reversing, as desired. As will be appreciated by those of skill in the art, although possible, it is not necessary to completely cease the monitoring/therapy operation of the AED during incident review. Monitoring that occurs while historical incident data is displayed may be referred to as "background monitoring" or "passive monitoring." In a preferred embodiment, the device continues to monitor patient condition in the background, while displaying historical incident data for user review on the visual image generator 24. The advantage of background monitoring are that: (1) it enables the device to record continuous ECG information (or selected ECG information according to the operation protocol); and (2) it enables the shock advisory system to be engaged such that in the event a shockable rhythm is detected, the user is advised so that incident review mode can be terminated. In contrast, "monitoring" or "active monitoring" describes the device operation wherein currently measured ECG information is displayed on the LCD.

In an alternative embodiment, the incident review mode may be automatically activated without user activation of user input 28. For example, incident review mode may be activated in response to another event such as a change in battery, or a change of the input signal received by electrodes 16.

The electrotherapy device operating modes can include patient treatment (in which, e.g., a therapeutic pulse is delivered to a patient via energy delivery system 19), monitoring (in which, e.g., the patient's ECG is monitored), incident review function (wherein the defibrillator pauses the monitoring and treatment function in order to enable a user to review treatment history for a patient), and self-test mode (in which device 10 runs self-test procedures to determine its operating condition). In any of its operating modes, electrotherapy device 10 can communicate incident data with memory 22.

Figure 2:
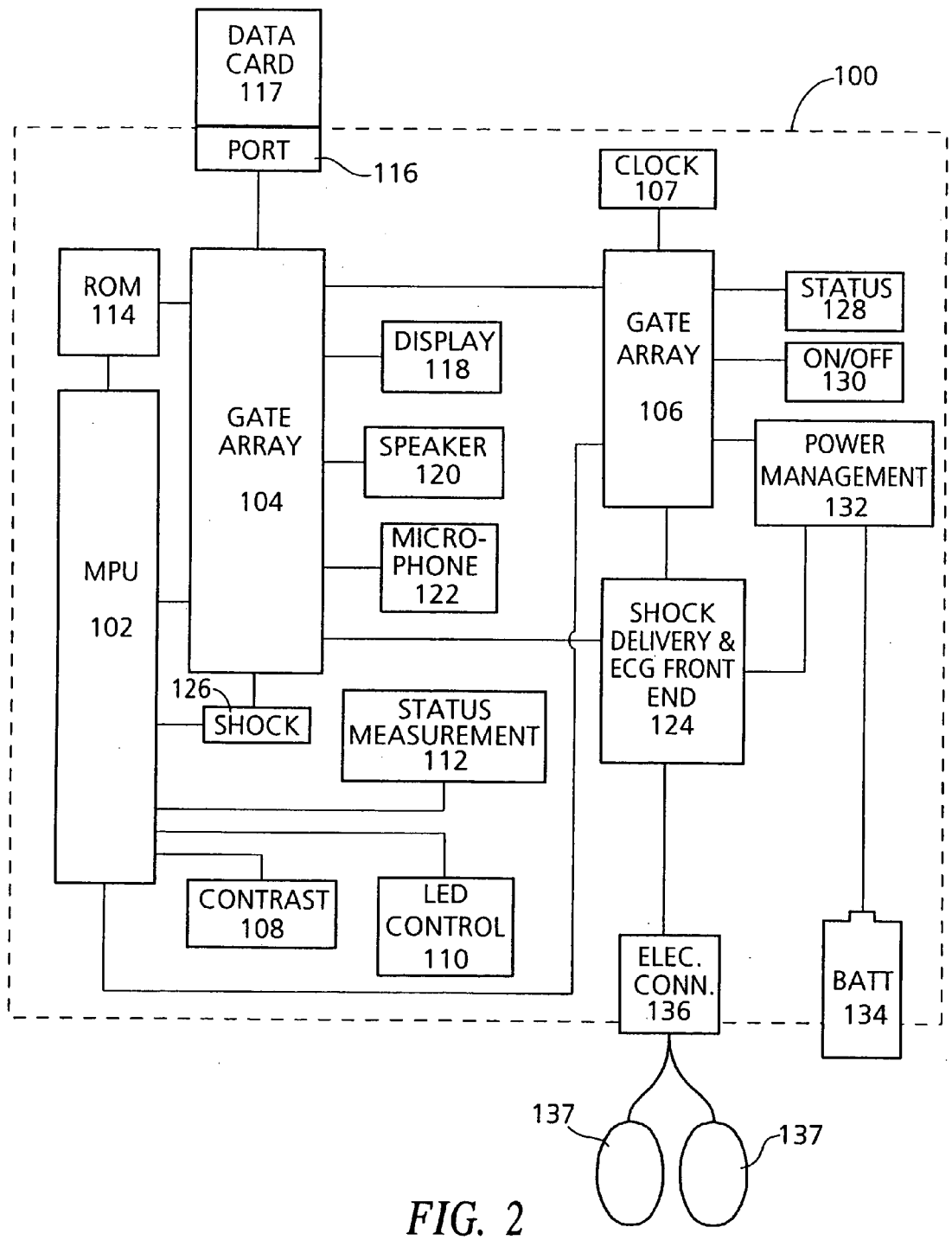
FIG. 2 is a block diagram of an external defibrillator useful for gathering incident data for use with the invention.

The major components of a semi-automatic external defibrillator according to a preferred embodiment are shown in FIG. 2 in block diagram form. Defibrillator control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112. MPU 102 also controls the operation of the display contrast button 108 while functioning as soft keys, such as when the device is in incident review mode.

Gate array 104 implements the memory map to system ROM 114, data card port 116 and other system memory elements. System ROM 114 is preferably flash ROM, although EPROM or any other electrically erasable and programmable nonvolatile memory could be used. Where a data card port 116 is provided as a means to enable patient data to be removed from the AED, it is preferable that a data card slot configured to interface with PC data cards conforming to the 1995 PC Card standard be provided.

For purposes of illustration, the device is described in terms of removable memory for recorded incident data, such as discrete event or ECG data. For purposes of writing to a removable memory device, such as a data card, gate array 104 provides the interface and control between defibrillator 100 and a data card 117 attached to data card port 116. For example, gate array 104 contains a FIFO buffer to compensate for differences between the speed with which ROM 114 can be accessed by MPU 102 and the speed with which the memory portion of data card 117 can be accessed. Gate array 104 also controls a display 118, a speaker 120, and a microphone 122. Gate array 104 can actuate a relay within the shock delivery and ECG front end system 124 in response to actuation of a shock button 126 by a user during treatment mode.

Gate array 106 receives time information from clock 107. Gate array 106 also provides a system monitor function by performing automatic self-tests of the defibrillator and its components. The gate array 106 displays the operational status of the defibrillator on a status display 128. Gate array 106 is also the defibrillator's interface with a user-activated on/off switch 130.

Gate array 106 controls the power management subsystem 132 to provide power to operate system components from battery 134 and to provide energy to the shock delivery system's capacitor(s) for a therapeutic shock during treatment mode. Gate array 106 also interfaces with the defibrillator's ECG front end 124, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators" and U.S. Pat. No. 5,607,454 to Cameron et al. for "Electrotherapy Method and Apparatus," the disclosures of which are incorporated herein by reference.

These defibrillator components communicate with each other over suitable communication buses.

As discussed above, incident data may be stored in memory located within the defibrillator 100. For example, suitable memory would include SRAM, flash memory, or an internal disk drive. Memory may be incorporated into the defibrillator or removable.

As is known in the art, the external defibrillator 100 can be operated in different modes, such as self-test mode, stand-by mode and patient treatment and monitoring mode. Further discussion of the operation of an external defibrillator in self-test mode, stand by mode and patient treatment mode is provided in, for example, U.S. Pat. No. 5,800,460, to Powers et al. for "Method for Performing Self-Test In A Defibrillator," the specification of which is incorporated herein.

During patient treatment and monitoring mode, the defibrillator receives ECG information from a patient through electrodes 137. The defibrillator then analyzes the ECG information to determine whether a therapeutic shock is advised. In a semi-automatic external defibrillator, a shock is delivered to the patient through the electrodes if a shock is advised and if the shock button 126 is actuated by a user. In a fully automatic external defibrillator, a shock would be delivered to the patient without further user intervention.

This information and sequence of events is stored by the defibrillator in memory, such as data card 117. In addition to recording patient ECG information, and defibrillator operation information, the defibrillator may also record other information (such as ambient sounds received by microphone 122).

The incident data collected by an external defibrillator (such as the defibrillator of FIG. 2) in patient treatment mode according to a preferred embodiment of this invention includes the following: defibrillator power on; defibrillation pads on or off; patient ECG; artifact detection; shock advised; no shock advised; charge begun; charge complete; device armed; device disarmed; shock initiated; shock delivered; shock aborted; pause for CPR; pause ended; manual override; manual charge; manual timeout; device off; low battery; depleted battery; critical error detected; non-critical error detected; audio (e.g., voice). The defibrillator may also obtain time information from, for example, the defibrillator clock, and/or the clock on the memory device, and store the time information with the incident data.

In one specific example, when using the defibrillator of FIG. 2, the recording process begins when the defibrillator is turned on. ECG data is recorded after defibrillation electrodes or pads are attached to the patient and previously recorded ECG memory is erased unless the defibrillator determines that there is continuous use, in which case the recorded data is appended to the previously recorded data. Continuous use may be determined where, for example, the device is turned off to replace the battery. In this example, the defibrillator may be programmed to recognize a power off of less than 5 minutes as a continuous use.

After the defibrillator has been used to treat a patient by, for example, a first responder and a set of incident data has been recorded, the recorded data can be reviewed on-screen by a subsequent caregiver.

In one embodiment, during incident review mode, shock delivery and ECG front end 124 are disabled by gate array 106 thus discontinuing the monitoring and therapy function of the defibrillator. Gate array 104 and microprocessor (MPU) 102 in turn communicate with memory, shown as data card 117, to retrieve recorded data for the incident. The data is then replayed on display 118. If the data is replayed along with the audio recording of the incident, then gate array 104 provides the audio information to speaker 120. In a preferred embodiment, during the incident review mode, a legend will appear on the display indicating that the device is in incident review mode (see, for example, FIG. 3). In an alternative embodiment, during incident review the shock delivery system is disabled, but gate array 106 continues monitoring the patient condition in the background.

It will be appreciated by those of skill in the art that a subsequent caregiver may or may not desire to review the audio recording along with the ECG. In a preferred embodiment, a subsequent caregiver will be given the opportunity to decide whether he or she wishes to review the audio data. While in incident review mode, the subsequent caregiver may fast forward or reverse through the ECG in order to more quickly access portions of the ECG data that are of interest, for example ECG response to a delivered shock. MPU 102 interfaces with the buttons 108 which may function as soft keys enabling the user to scroll quickly through the recorded incident data. Alternatively MPU 102 may interface with a set of dedicated control buttons (not shown) which activate or terminate the incident review mode, as well as fast-forward or reverse through the recorded incident data.

The caregiver may resume active monitoring and treatment mode after terminating the incident review mode. In this instance, shock delivery and front end 124 are reactivated. Alternatively, the caregiver may end the therapy session for the defibrillator altogether.

Where monitoring was discontinued during incident review, the defibrillator again begins recording incident information in memory when incident review mode is ended. In this instance, incident recording would be, for example, resumed following the last recorded incident for the patient and an annotation could appear indicating that treatment and therapy mode was paused for incident review. Thus, when a caregiver ends the incident review mode in the middle of replaying the incident, subsequent recording of patient ECG would append to the previously recorded incident data.

As will be appreciated by those of skill in the art, the incident review mode can be activated and terminated in a variety of ways. For example, dedicated buttons may be provided for that purpose, soft keys may be provided, the on/off button may also function to enable incident review, or the battery insertion may be set-up to activate the incident review. Importantly, where monitoring continues in the background a mechanism should be employed that enables the user to quickly end the review mode and return to the therapy mode in response to an arrhythmia. An appropriate mechanism would be, for example a dedicated user activation button. Alternatively, it may be desirable to automatically return to active monitoring/therapy mode in response to a detected arrhythmia. Other mechanisms for activating the incident review may also be employed without deviating from the scope of the invention.

Figure 3:
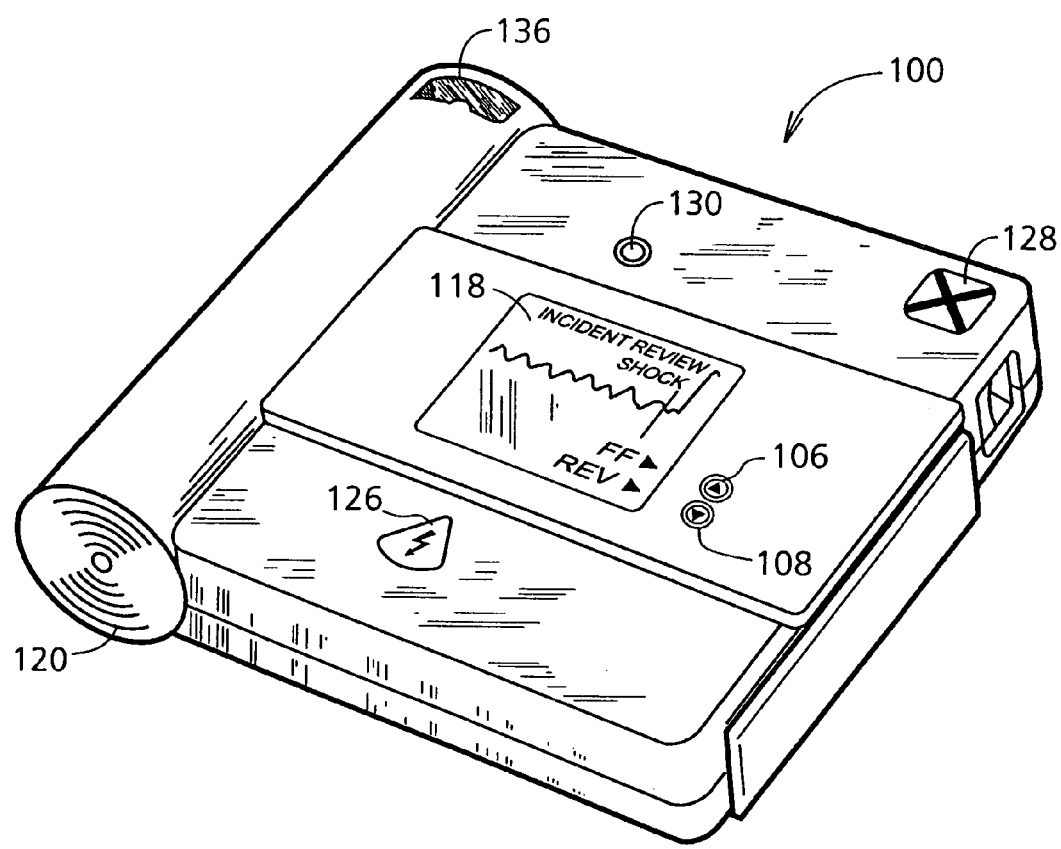
FIG. 3 is a top elevational view of a defibrillator with a display screen that enables a user to replay incident data.

FIG. 3 illustrates a defibrillator according to the invention which is in incident review mode. Contrast buttons 108 are functioning as soft-keys to enable the user to quickly navigate through the recorded incident data while in incident review mode. An annotated ECG is shown on LCD screen 118. The annotated ECG indicates "shock" and the location within the ECG where the shock was delivered. A legend also appears, in this case along the top, indicating that the device is in incident review mode. Of course as will be appreciated by those of skill in the art, the LCD display may display both the historical data along with the currently monitored ECG data. In such an embodiment, it would be important to provide a mechanism for distinguishing between the historical data and the current data. Such a mechanism could include, for example: a legend, color coding of the ECG, etc.

Figure 4:
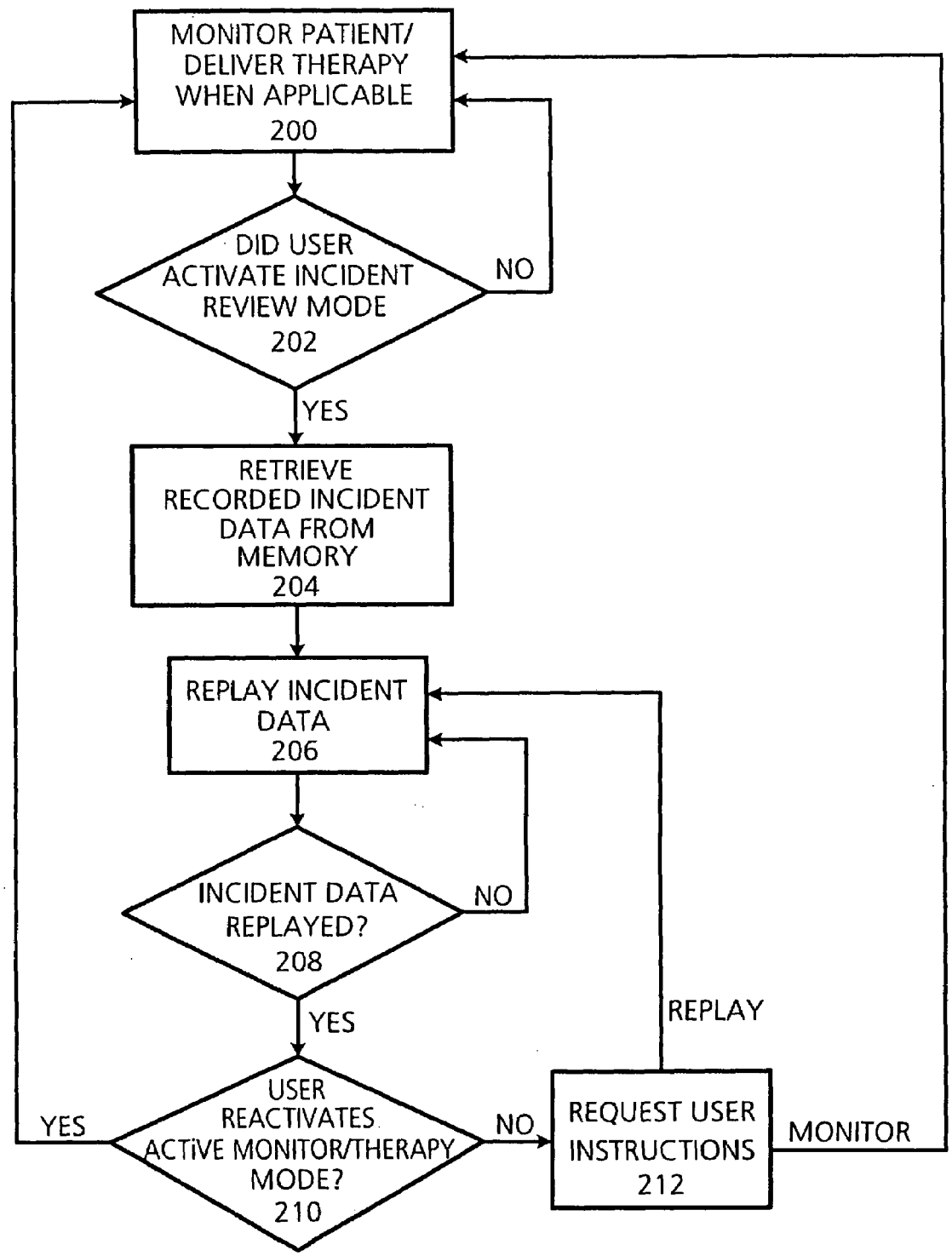
FIG. 4 is a flow chart demonstrating the operation of an AED capable of replaying incident data.

FIG. 4 is a flow chart that demonstrates an example of operation of the AED. As shown by block 200, the AED is in monitor/therapy mode. While in this mode the AED monitors patient ECG and, when appropriate, delivers therapy (for example, when VF is detected). If the user has not activated incident review mode 202, then the defibrillator continues to monitor the patient. If the user does activate the incident review mode 202, then the recorded incident data is retrieved from memory 204. Once the recorded incident data is retrieved from memory, the data is displayed on the device screen. As will be appreciated by those of skill in the art, the incident review may either be automatically displayed after the recorded incident data is retrieved from memory or may require further user activation to begin the display. Further, as described above, monitoring may continue in the background during incident review mode.

Once the incident data has been replayed 208, then the user may reactivate the monitor/therapy mode 210. If the user does not activate the monitor therapy mode, the AED will request further instructions 212. At this point the user may either instruct the defibrillator to return to monitor/therapy mode 200 or may begin to replay the recorded incident data 206. As discussed previously, where the defibrillator continues to monitor patient condition in the background, mechanisms may be provided to end the incident review mode in response to a detected arrhythmia—either by user activation or automatically.

Of course, the operation of this feature is also applicable to devices where the monitor/therapy modes are not combined. For example, where the user is required to intervene in order to activate the monitor function.

It should be appreciated that the scope of the invention is not limited to the embodiments described above. Various modifications and alterations might be made by those of skill in the art without departing from the scope and spirit of the present invention.

What is claimed is:

1. A method of reviewing incident data on an external defibrillator having a screen, comprising:
   deploying the defibrillator for use in an emergency, wherein the defibrillator is attached to a patient;
   monitoring ECG data from the patient;
   recording the monitored ECG data in memory; and
   activating an incident review mode in which the previously recorded ECG data stored in memory and the currently monitored information are displayable simultaneously on the defibrillator screen of the defibrillator while the patient is being monitored by the defibrillator without the need to attach the defibillator to another external device for display, and said recorded ECG data also being displayable offline.

2. The method of claim 1 further comprising:
   retrieving the recorded ECG data from memory; and
   replaying the recorded ECG memory on a visual image generator.

3. The method of claim 1 wherein the activating step is accomplished by user intervention.

4. The method of claim 2 wherein the replaying step occurs automatically without user actuation of an activation button.

5. The method of claim 1 wherein the recording step includes recording audible data received from a microphone into memory.

6. The method of claim 2 wherein the replaying step further comprises replaying audible data recorded into memory during the recording step.

7. The method of claim 2 wherein prior to the replaying step, a user select which information is replayed.

8. The method of claim 7 wherein the user selects from the group consisting of: ECG data, audible data, and a combination of ECG and audible data.

9. The method according to claim 1 wherein the ECG data is selected from the group consisting of: patient ECG data and patient data therapy.

10. The method of claim 2 wherein the replaying step is activated by the user depressing soft keys.

11. The method of claim 2 wherein the replaying step is activated by the user depressing a combination of soft keys.

12. The method of claim 1 wherein the incident review mode is activated in response to disconnecting the patient from the defibrillator.

13. The method of claim 1 wherein the incident review mode is activated in response to insertion of a battery.

14. The method of claim 1 further comprising the step of displaying a legend on a visual image generator that the defibrillator is event review mode.

15. The method of claim 2 wherein the replaying is optional and the replaying option is presented to a user when the defibrillator is turned off.

16. The method of claim 2 wherein the replaying is optional and the replaying option is presented to the user when a battery is inserted into the defibrillator.

17. The method of claim 2 wherein the replaying step further comprises displaying currently monitored ECG data along with the recorded ECG data retrieved from memory.

18. An external defibrillator comprising:
    a controller;
    an energy delivery system operable by the controller to deliver an electrical shock from an energy source to an electrode interface;
    memory for recording incident data;
    a screen;
    an incident review activator; and
    an incident review output comprising a visual image generator, wherein the incident review output retrieves the incident data from memory upon activation of the incident review activator by the user and simultaneously displays the retrieved incident data on the defibrillator screen and the current patient monitoring while the patient is being monitored by the defibrillator without requiring communication with an external device.

19. The external defibrillator of claim 18 wherein the incident review output also comprises an audible sound generator.

20. The external defibrillator of claim 19 wherein the memory is selected from the group consisting of: flash, EEPROM, ROM and RAM.

21. The external defibrillator of claim 19 wherein the incident review output also comprises an audible sound generator.

22. The external defibrillator of claim 18 wherein the incident review activator is a soft key.

23. The external defibrillator of claim 18 wherein the incident review activator is a combination of soft keys.

24. The external defibrillator of claim 18 wherein the defibrillator further comprises incident review navigators.

25. The external defibrillator of claim 23 wherein the incident review navigators enable a caregiver to advance or replay the incident.

26. The external defibrillator of claim 25 wherein the incident review navigator is a soft key.

27. The external defibrillator of claim 25 wherein the incident review navigator is a combination of soft keys.

* * * * *